(12) United States Patent
Valencia et al.

(10) Patent No.: US 6,371,940 B1
(45) Date of Patent: Apr. 16, 2002

(54) CATHETER RAPID EXCHANGE DEVICE

(75) Inventors: Carlos A. Valencia, Hialeah; Federico Frigerio, Miami; Giovanni Acocella, Miami; Alejandro Nasio, Miami, all of FL (US)

(73) Assignee: Mark Two Engineering, Inc., Miami, FL (US)

( * ) Notice: Subject to any disclaimer, the term of this patent is extended or adjusted under 35 U.S.C. 154(b) by 0 days.

(21) Appl. No.: 09/516,391

(22) Filed: Mar. 1, 2000

(51) Int. Cl.[7] .............................................. A61M 5/178
(52) U.S. Cl. ............................ 604/164.13; 604/165.02; 600/585
(58) Field of Search ...................... 604/164.01, 164.13, 604/165.01, 165.02, 178, 523, 528; 600/585

(56) References Cited

U.S. PATENT DOCUMENTS

| | | | |
|---|---|---|---|
| 4,762,129 A | | 8/1988 | Bonzel |
| 5,031,636 A | * | 7/1991 | Gambale et al. |
| 5,040,548 A | | 8/1991 | Yock |
| 5,269,759 A | | 12/1993 | Hernandez et al. |
| 5,827,241 A | | 10/1998 | Douk et al. |
| 6,099,547 A | * | 8/2000 | Gellman et al. |

FOREIGN PATENT DOCUMENTS

EP 0747081 A2 11/1996

* cited by examiner

*Primary Examiner*—Jeremy Thissell
(74) *Attorney, Agent, or Firm*—David P. Gordon; David S. Jacobson; Thomas A. Gallagher (57) ABSTRACT

A mechanical rapid exchange device is provided which plastically deforms a guidewire and constrains the guidewire in a non-linear configuration such that a catheter may be moved relatively proximally or distally over the guidewire to facilitate catheter exchange. The device generally includes a housing having a channel along a length of one side of the housing, a central first punch movable between a first position in which the first punch is located substantially to one side of the channel and a second position in which it extends at least partially into the channel, lateral second and third punches movable between a respective first position in which they are located to the other side of the channel and a respective second position in which they extend at least partially into the channel. The device also includes a handle attached via levers to the second and third punches such that when the handle is actuated, the second and third punches are moved into the second position. A plastically deformable support tube extendable over a exterior portion of a guidewire and positionable within the channel is also provided.

23 Claims, 6 Drawing Sheets

CATHETER RAPID EXCHANGE DEVICE

BACKGROUND OF THE INVENTION

1. Field of the Invention

This invention relates broadly to surgical devices. More particularly, this invention relates to devices for an over-the-guidewire exchange of one catheter for another in the human body.

2. State of the Art

Catheterization procedures are well known for diagnosis and therapy of lesions in the cardiovascular system. One such procedure is angioplasty, for eliminating or ameliorating the vascular blockage or constriction in blood vessels associated with supplying blood to the heart or other organs. In an angioplasty procedure, an expandable balloon carried by an elongated catheter is introduced into the arterial system of a patient and advanced until it is positioned in the region of the blockage or constriction. Once so positioned, the balloon is expanded by filling it with a liquid. In successful procedures, the expandable balloon presses outwardly against the walls of the artery and expands the artery to a degree to which the artery is either partially or completely reopened to blood flow.

Prior to initiating the angioplasty procedure, a guiding catheter is placed, typically via the femoral artery, into the aorta and its tip is engaged into the coronary arteries which branch from the aorta. Once placed, the guiding catheter acts as a conduit to access the coronary arteries with a guidewire and balloon catheter. The guiding catheter is a portion of plastic tubing having a length of about 95 centimeters, an inside diameter of about 2 millimeters, and an outside diameter of about 2.5 millimeters. A hemovalve, i.e., a valve preventing blood loss through the guiding catheter when a tubular conduit such as a balloon catheter is passed therethrough, is provided at the proximal end of the guiding catheter.

Then, external of the patient, the physician threads a guidewire through a balloon catheter. The guidewire is a piece metal wire, e.g., titanium or nickel-titanium alloy wire, approximately 175 centimeters in length, and about 0.25 to 0.46 millimeters in diameter. The soft distal tip of the guidewire is often shaped to form a "J" configuration. This "J" shape allows the physician to steer the guidewire by twisting its proximal end while advancing or retracting the guidewire. The balloon catheter is an elongate flexible plastic tubular member defining two longitudinal passages and having a balloon located at or adjacent its distal end. One longitudinal passageway defines a conduit through which the guidewire can be passed. The other longitudinal passage defines a conduit in fluid communication with the interior of the balloon and through which inflation fluid can be injected to inflate the balloon.

Among the types of balloon catheters is one in which the two longitudinal passages are generally side by side and parallel. In another type of balloon catheter, the two longitudinal passages are coaxial. In this latter type, the guidewire is passed down the inner passage and the inflation fluid is injected into the balloon via the outer passage. Balloon catheters, as well as associated apparatus and their method for use in angioplasty, are generally described in U.S. Pat. No. 5,040,548 to Yock, which is hereby incorporated by reference herein in its entirety.

The physician passes the guidewire through the appropriate one of the longitudinal passages in the balloon catheter, leaving a portion of the guidewire extending from the distal and proximal ends of the balloon catheter. This assembly is then inserted through the hemovalve and into the proximal end of the guiding catheter, distal end first. The assembly is inserted until the balloon which is attached at or near the distal end of the balloon catheter is near the distal end of the guiding catheter. At this point, the physician, while maintaining the balloon catheter stationary, pushes on the guidewire to advance it outwardly from the distal end of the guiding catheter.

The physician steers the guidewire into the chosen one of the coronary arteries, and advances it until it reaches a location of constriction which the physician desires to open. Carefully, the physician eases the distal end of the guidewire through the region of constriction until the guidewire tip is on the opposite side of the constriction relative to the guiding catheter.

With the guidewire held stationary, the physician advances the balloon catheter over the guidewire until it is located in the region of constriction of the artery. Then, with the balloon held stationary, inflation fluid is injected into the conduit which communicates with the balloon, causing it to inflate. Inflation of the balloon expands the walls of the artery in the region of constriction and, in successful procedures, opens the artery to sufficient blood flow.

Arteries vary in size, and therefore balloon catheters having balloons of different sizes are provided for selection by the physician. These balloons, when inflated, range from about 1.5 millimeters to about 4 millimeters in diameter. Sometimes, it is necessary for the physician to use more than one balloon to open an artery, as in some instances, the chosen balloon may be too large to be advanced into the constricted area, or in other instances, the first chosen balloon size, even when inflated, is not large enough to open the constricted area to the degree desired. In such cases, it is necessary to exchange one balloon catheter for another during the same angioplasty procedure.

In order to accomplish this exchange, the guidewire is left in place, and the balloon catheter is withdrawn entirely from the guiding catheter until it is completely disengaged from the proximal end of the guidewire. A new balloon catheter, having a different sized balloon, is then reinserted over the guidewire and advanced back to the location of the constricted area, where it is used to effect the desired result.

It is highly desirable to leave the guidewire in position; i.e., once the guidewire is passed through the constricted area, preferably the guidewire remains extending through the constriction for the duration of the angioplasty procedure. This means that the guidewire must remain in place even during the exchange of balloon catheters. The reason for this is that when a foreign object, such as the guidewire, is introduced into an artery, the artery walls sometimes go into spasm, and constrict the artery generally along a substantial portion of its length. If the artery tends to contract in this way, removal of the guidewire while the artery is so contracted will sometimes render it virtually impossible to reinsert the guidewire through the contracted artery.

Withdrawal of the balloon catheter without dislocating the guidewire is a difficult and cumbersome procedure, requiring both a second individual, in addition to the physician, and the attachment of a removable extension to the proximal end of the guidewire. Attachment of the extension to the guidewire during withdrawal of the balloon catheter is necessary because, if the balloon catheter were withdrawn over the proximal end of the guidewire, there would be no way that the guidewire could be manually held stationary. The extension is required to provide a proximal end of the guidewire which will extend outwardly from the proximal end of the balloon catheter even when the balloon catheter is entirely withdrawn from the patient. Even with the extension, the physician must enlist the aid of an assistant to manually hold stationary the proximal end of the guidewire, preventing guidewire movement, while the physician withdraws one balloon catheter and inserts a replacement balloon catheter. This is a cumbersome and awkward procedure at best.

One solution to this difficult procedure is provided in U.S. Pat. No. 4,762,129 to Bonzel. Bonzel discloses a balloon catheter having a single lumen for inflation fluid and a balloon at the distal end of the catheter. The balloon has two passages: a first passage in fluid communication with the lumen of the balloon catheter to inflate the balloon and a second passage for receiving a guidewire therethrough. A guidewire extends externally alongside the balloon catheter and passes through the second passage and beyond the distal end of the balloon. As a result, once the distal end of the guidewire is passed through the vascular constriction, the proximal end of the guidewire may be manually held in position and the balloon may ride over the guidewire into the constriction. If needed, the balloon catheter can be withdrawn over the guidewire and a new balloon catheter may then be advanced over the guidewire to the locus of constriction. Nevertheless, the Bonzel device has several serious drawbacks. First, as hemovalves are generally designed to have a single tubular conduit extend therethrough, the geometry of the side-by-side extension of both the guidewire and the balloon catheter through the hemovalve prevents a fluid tight seal from forming about the balloon catheter-and guidewire. Therefore, use of the Bonzel apparatus results in increased blood loss from the patient. Second, the device requires substantially constant fluoroscopy or x-ray use, as the physician must be careful not to proximally displace the guidewire relative to the balloon such that guidewire is withdrawn from the second passage of the balloon. It will be appreciated that if the guidewire is completely removed from the second passage of the balloon while the guidewire and balloon catheter are located in situ, it is nearly impossible to reinsert the guidewire therethrough. Third, if the physician desires to exchange one guidewire for another (e.g., a stiffer guidewire for a more flexible guidewire), which is possible with balloon catheters having two conduits provided therein, the physician similarly faces the problem of not being able to insert the new guidewire through the second passage of the balloon. As such, the physician is limited to using the guidewire with which he or she began the interventional or diagnostic procedure.

A second solution is provided in co-invented U.S. Pat. No. 5,269,759 to Hernandez et al. which discloses an exchange device having a magnetic element and a guidewire provided with a magnetic portion. Magnetic forces are able to hold the guidewire fixed relative to the exchange device, permitting a first balloon to be withdrawn over the guidewire, and a second balloon to be advanced in replacement. However, the magnetic exchange device also has several drawbacks. First, it requires the use of high cost guidewires having magnetic elements. Second, magnetic guidewires tend to be more fragile than other guidewires due to undercuts in the guidewires for magnet placement. Third, magnetic guidewires have relatively poor steerability. Fourth, magnetic wires are more corrosive than non-magnetic guidewires.

Yet another solution is provided in U.S. Pat. No. 5,827,241 to Douk et al., which is hereby incorporated by reference herein in its entirety, in which it is disclosed that the position of a guidewire within the body can be maintained by constraining coextensive segments of the catheter and the guidewire in a non-linear configuration outside the body. The non-linear configuration is such that when the catheter is moved relative to the guidewire, the frictional force between the catheter and the guidewire is less than the force required to move the guidewire through the non-linear configuration. Therefore, as the catheter is advanced or withdrawn from the body, axial movement of the guidewire relative to the catheter is inhibited. While This teaching appears to suggest a good solution, it has not been commercially exploited due to the difficulties in implementing the teaching in a suitable device which quickly, easily and inexpensively plastically deforms the guidewire such that the catheter can then be moved relative thereto.

SUMMARY OF THE INVENTION

It is therefore an object of the invention to provide an exchange device which constrains coextensive segments of a catheter and a guidewire in a non-linear configuration.

It is an another object of the invention to provide an exchange device which plastically deforms the guidewire.

It is also an object of the invention to provide an exchange device which is unobtrusive and may be positioned adjacent the surgical field.

It is a further object of the invention to provide an exchange device which is easy to use.

It is yet another object of the invention to provide an exchange device which is relatively inexpensive to manufacture and disposable.

In accord with these objects, which will be discussed in detail below, a mechanical rapid exchange device is provided which plastically deforms a guidewire and constrains the guidewire in a non-linear configuration such that a catheter may be moved relatively proximally or distally over the guidewire to facilitate catheter exchange. The device generally includes a housing having a channel along a face of one side of the housing, a center punch movable between a first position in which the center punch is located substantially to one side of the channel and a second position in which it extends at least partially into the channel, two lateral punches movable between a respective first position in which they are located to the other side of the channel and a respective second position in which they extend at least partially into the channel. The device also includes a handle attached via levers to the lateral punches such that when the handle assembly is actuated, the lateral punches are moved into the second position. A plastically deformable support tube extendable over a portion of a guidewire and positionable within the channel is also provided.

In use, the plastically deformable support tube is positioned over an exterior portion of the guidewire (outside the human body), and the support tube is then positioned within the channel. The center punch is then moved into the channel and into its second position, i.e., against the support tube, and locked in position. The handle is next actuated, such that the lateral punches enter the channel from the side opposite the center punch and bend the support tube and guidewire about the center punch such that the support tube and guidewire are each plastically deformed into a non-linear configuration. When the handle is returned to its linear position, the lateral punches return to a position outside the channel, and the center punch, locked in position, prevents the deformed support tube from sliding axially within the channel of the housing. The non-linear configuration of the support tube is shaped such that when a catheter, e.g., a balloon catheter, is moved over the guidewire and through the support tube, the frictional force between the catheter and the guidewire is less than the force required to move the plastically deformed guidewire through the stationary support tube. Therefore, as the catheter is advanced or withdrawn through the support tube, axial movement of the guidewire relative to the support tube is prevented. A catheter may then be fed over the guidewire and into the support tube, i.e., between the support tube and the guidewire, while the guidewire is held in position by a physician or an assistant who holds the housing of the device. As such, withdrawing of a catheter over the guidewire and placement of a new catheter over the guidewire is facilitated.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
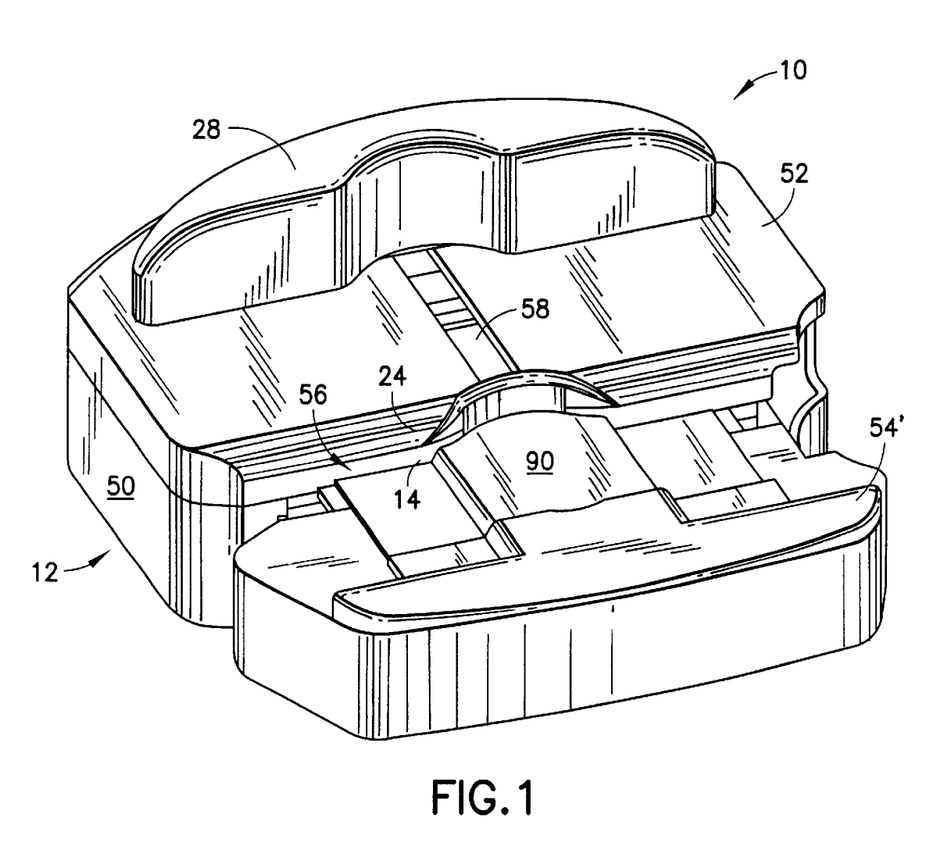
FIG. 1 is a top perspective view of a mechanical exchange device according to the invention.
Figure 2:
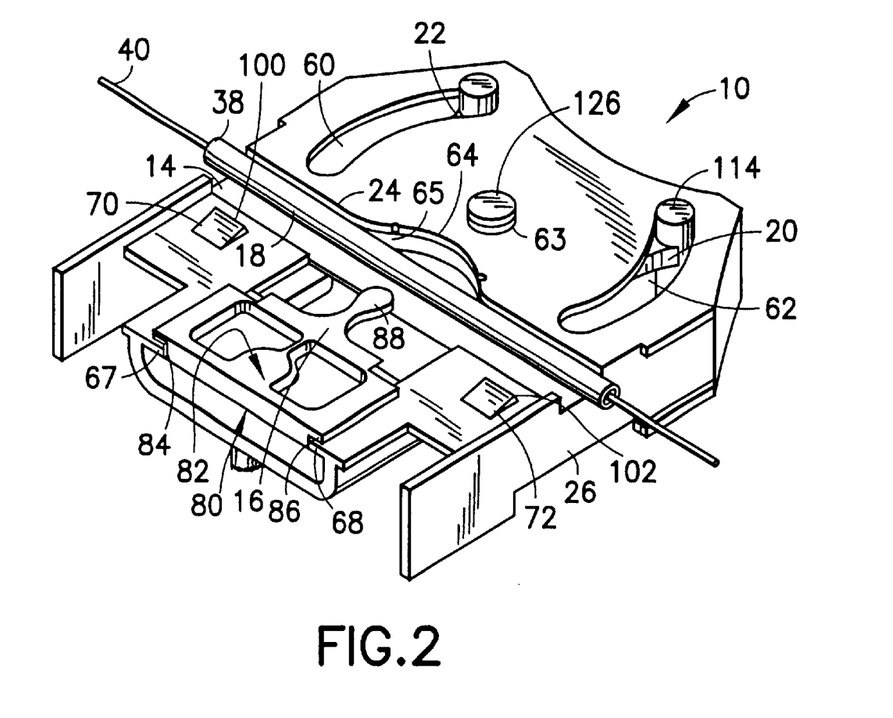
FIG. 2 is a partial top perspective view of the mechanical exchange device, shown in a non-actuated configuration with a support tube and guidewire positioned within a channel of the device.
Figure 3:
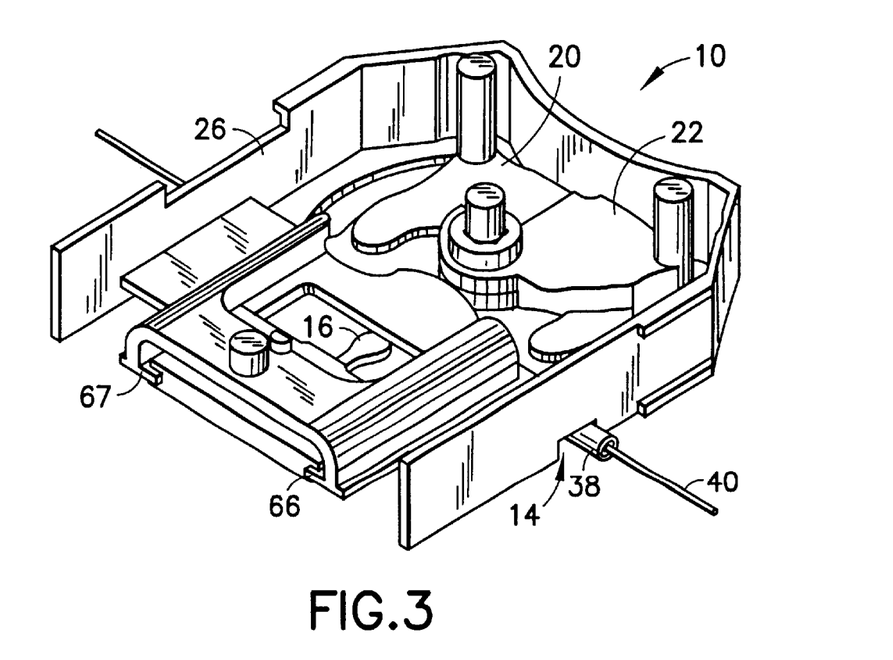
FIG. 3 is a partial bottom perspective view of the mechanical exchange device, shown in a non-actuated configuration with a support tube and guidewire positioned within a channel of the device.
Figure 4:
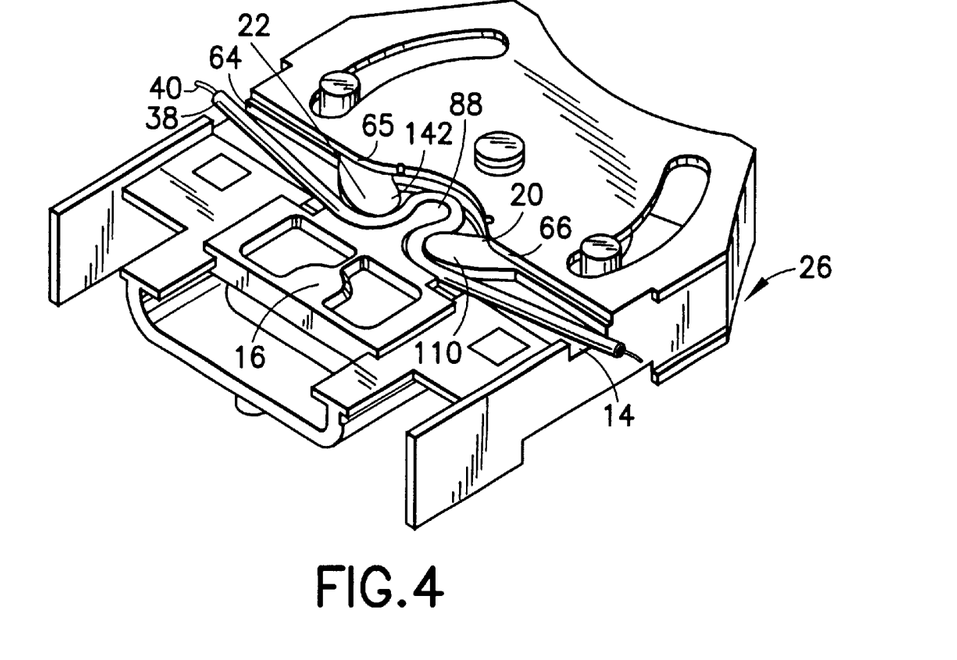
FIG. 4 is a partial top perspective view of the mechanical exchange device, shown in an actuated configuration with a support tube and guidewire positioned within a channel of the device.
Figure 5:
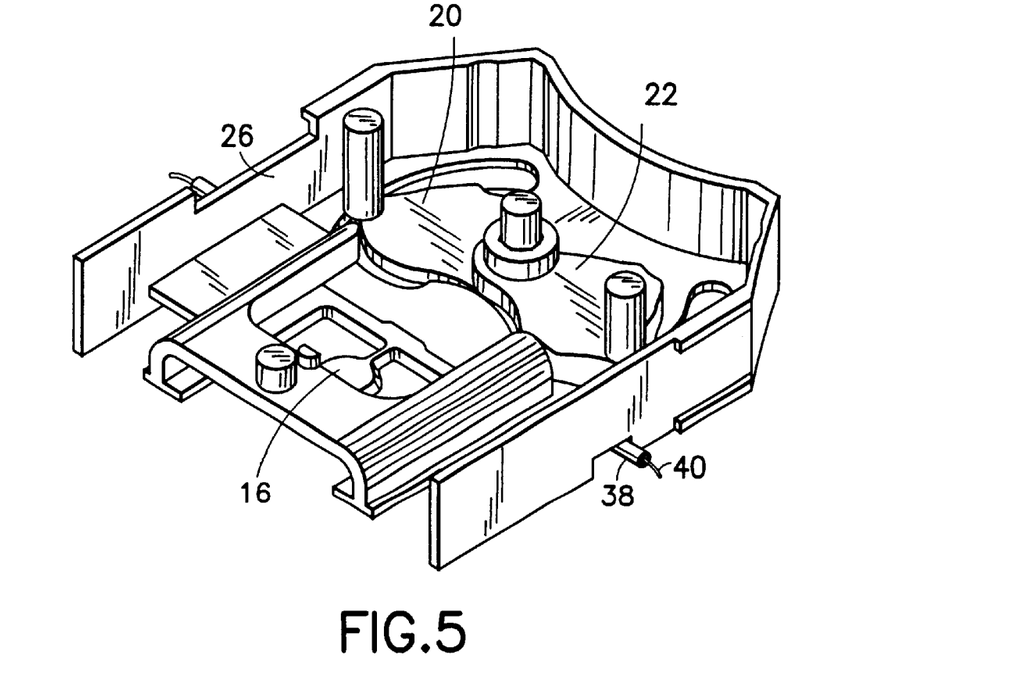
FIG. 5 is a partial bottom perspective view of the mechanical exchange device, shown in an actuated configuration with a support tube and guidewire positioned within a channel of the device.
Figure 6:
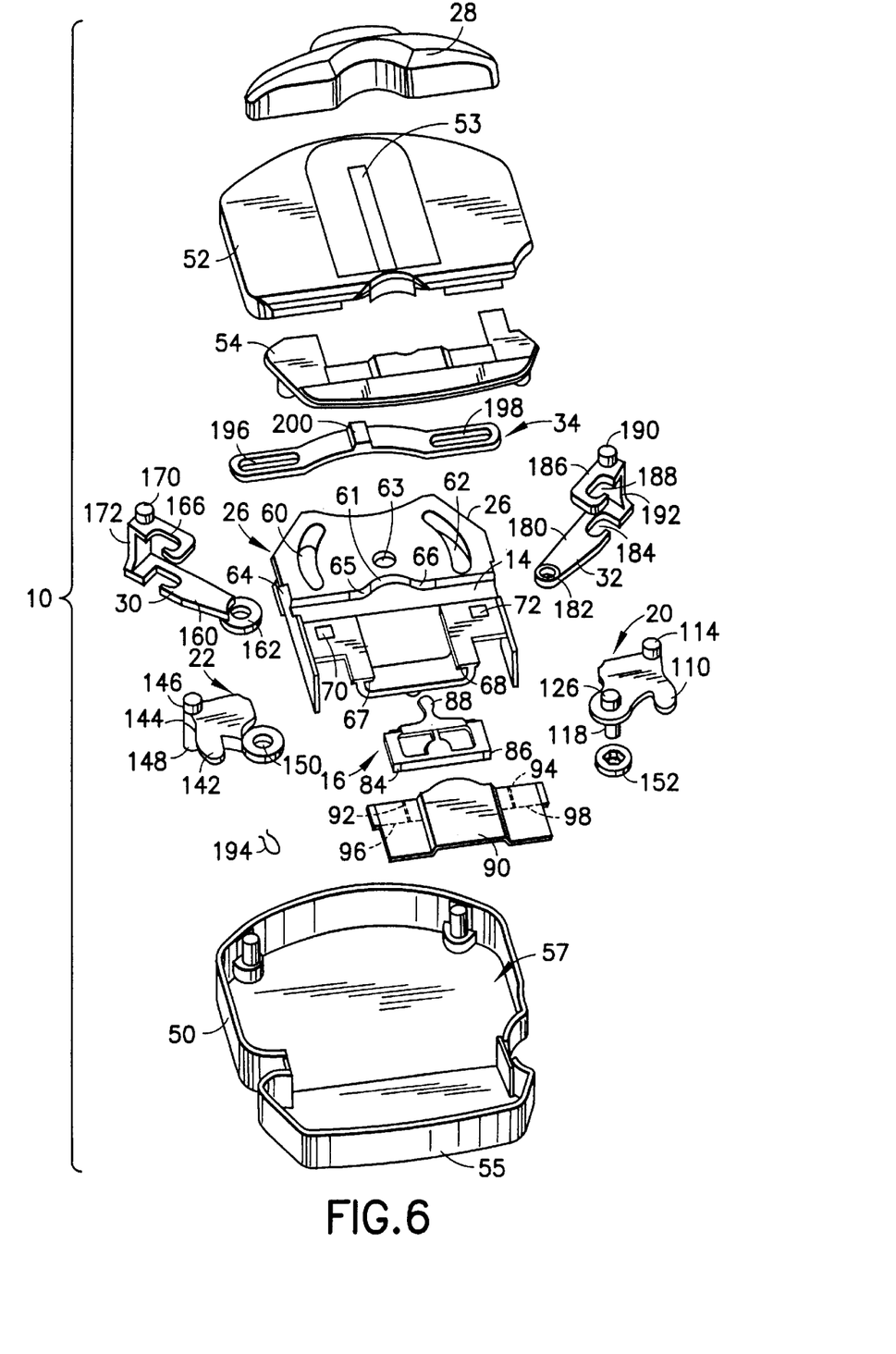
FIG. 6 is an exploded perspective view of the mechanical exchange device.

Turning now to FIGS. 1 to 6, a mechanical catheter exchange device 10 generally includes a housing 12 having an opening into a channel 14 along a face of one side of the housing (FIG. 1), a center punch 16 movable between a first position in which the center punch is located substantially to one side 18 of the channel 14 (FIG. 2) and a second position in which it extends at least partially into the channel (FIG. 4), first and second lateral punches 20, 22 movable between a respective first position in which they are located to the other side 24 of the channel 14 (FIGS. 2 and 3), opposite the center punch, and a respective second position in which the lateral punches extend at least partially into the channel (FIGS. 4 and 5). An assembly frame 26 is provided within the housing 12 and defines the channel 14. In addition, the punches 16, 20, 22 are movably coupled to the assembly frame (FIGS. 3, 5 and 6). The device 10 also includes a handle 28 attached via levers 30, 32 and lever joiner 34 (FIG. 6) to the lateral punches 20, 22 such that when the handle 28 is moved, the lateral punches 20, 22 are moved into the second position. A plastically deformable support tube 38 extendable over a portion of a guidewire 40 and is also provided and positionable within the channel 14.

More particularly, the housing 12 includes first, second, and third shell portions 50, 52, 54 between which the components of the device 10, except the handle 30, are generally located. The first shell portion 50 includes a base 55 and defines a tray 57 in which the assembly frame 26 is seated. The second and third shell portions 52, 54 are secured to the first shell portion 50 and enclose the assembly frame 26. In addition, the second and third shell portions 52, 54 are spaced apart and define a space 56 which provides an opening into the channel 14 (FIG. 1). The second shell portion 52 also defines a medial slot 58, through which the handle 28 is coupled to the lever joiner 34, as described in more detail below.

Referring to FIGS. 2 and 6, as stated above, the assembly frame 26 substantially defines the channel 14. More particularly, the channel is preferably substantially linear. Laterally, on one side of the channel 14, the assembly frame 26 includes two curved slots 60, 62 oriented generally perpendicular to the channel, and a pivot hole 63 medially therebetween. In addition, on the same side of the channel, a wall 64 partially defining the channel 14, includes two vertical slots 65, 66 which permit the lateral punches 20, 22 to extend therethrough into the channel, and a curving wall portion 61 therebetween, as described further below. To the other side of the channel, the assembly frame includes a set of medially directed guide rails 67, 68 on which the center punch 16 rides, as described below, and a set of ramps 70, 72 rising toward the channel.

Still referring to FIGS. 2 and 6, the center punch 16 includes a first (bottom) side 80, a second (top) side 82, lateral guide channels 84, 86, and a punch head 88. The lateral guide channels 84, 86 are sized to slide the center punch on the guide rails 67, 68 of the assembly frame 26. The head 88 preferably centrally located between the guide channels 84, 86, is preferably shaped as a flattened, teardrop. In addition, the head 88 is preferably formed as an extension of the top side 82 of the center punch.

Referring to FIG. 6, a sliding catch 90 is fixedly coupled to the center punch 16, e.g., by gluing or snap fit. Optionally, the sliding catch 90 and center punch 16 may be integrally molded together as a single component. The sliding catch 90 includes lower guide rails 92, 94 and catch walls 96, 98. The lower guide rails 92, 94 guide the sliding catch between the ramps 70, 72 of the assembly frame 26 when sliding force is provided to the sliding catch. As such, when the sliding catch 90 is moved relative to the assembly frame 26, the center punch 16 is likewise moved along the guide rails 67, 68 relative thereto. In addition, the catch walls 96, 98, once pushed over the ramps, prevents the sliding catch 16 from being retracted, as the catch walls abut against the drop surfaces 100, 102 (FIG. 2) of the ramps 70, 72 if the sliding catch is pushed rearward. Because the center punch 16 and sliding catch 90 are fixed relative to each other, when the sliding catch is locked against the drop surfaces 100, 102 of the ramps, the center punch 16 is likewise locked in position.

Figure 7:
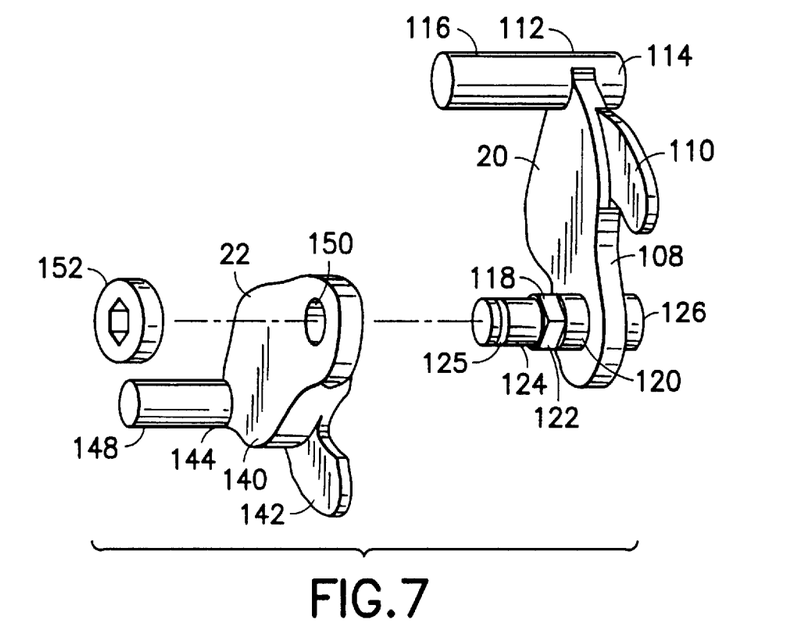
FIG. 7 is an exploded perspective view of the lateral punch assembly of the mechanical exchange device, viewed from a side opposite that shown in FIG. 6.

Turning now to FIGS. 6 and 7, the first lateral punch 20 includes a generally flat body 108 provided with a curved punch head 110, a first lever post 112 having a first portion 114 which extends on one side of the body and a second portion 116 which extends on the other side of the body. The first lateral punch 20 also includes a pivot post 118 including a cylindrical first portion 120 closest to the body, a second portion 122 having a non-circular cross-section, e.g., a hexagonal cross-section, and a cylindrical third portion 124. The third portion 124 is preferably provided with a circumferential channel 125. The first lateral punch additionally includes a pivot head 126 which is engaged within the pivot bore 63 of the assembly frame.

The second lateral punch 22 includes a generally flat body 140 provided with a curved punch head 142 curving in a direction opposite that of the head 110 of the first lateral punch 20. The second lateral punch 22 also includes a second lever post 144 having a first portion 146 which extends on one side of the body and a second portion 148 which extends on the other side of the body, and a pivot bore 150. The second lateral punch is rotatably coupled to the first lateral punch by positioning the pivot bore 150 of the second lateral punch over the first portion 120 of the pivot post 118 of the first lateral punch 20. A nut 152 provides an interference fit over the second portion 122 of the pivot post and prevents the release of the second lateral punch 22 from the first lateral punch 20. When the first and second lateral punches 20, 22 are rotated relative to each other, the curved heads 110, 142 are rotated through an arc relative to each other. The second portions 114 and 148 of the lever posts 112, 144 are positioned in the curving slots 60, 62, respectively, of the assembly frame 26 and when a force is applied to the lever posts 112, 144 via handle 28 and levers 30, 32 as described hereinafter in a direction normal to the channel 14, the lever posts are adapted to move longitudinally through the slots 60, 62.

Figure 8:
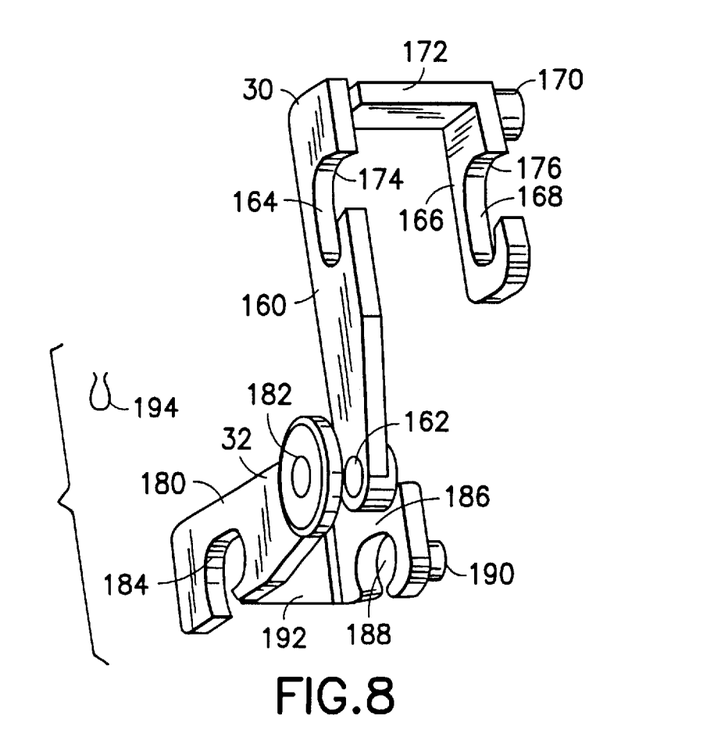
FIG. 8 is an exploded perspective view of the lever assembly of the mechanical exchange device viewed from the same side as FIG. 7.

As shown in FIGS. 6 and 8, the first lever 30 includes an elongate first arm 160 having a pivot bore 162 at one end, an intermediate first longitudinal rocker groove 164, a second arm 166 having a second longitudinal rocker groove 168 and a first cylindrical nub 170, and a connector portion 172 connecting the first and second arms 160, 166 in parallel such that the rocker grooves 164, 168 are aligned. The rocker grooves 164, 168 are each oblong shaped, and each have an opening 174, 176 along a side of the arm 160, 166 at an end nearest the connector portion 172. The connector portion 172 is sized to permit the first and second arms 160, 166 to extend on either side of (above and below) the assembly frame 26. The first lever 30 is positioned about the lateral punches 20, 22 and assembly frame 26 with the pivot bore 162 positioned over the third portion 124 of the pivot post 118. The first rocker groove 164 is engaged about the second portion 116 of guide post 112, with the opening 174 of the groove generally positioned downward, i.e., toward the channel 14. The connector portion extends the height of the assembly frame and positions the second arm 166 such that the second rocker groove 168 is engaged about the first portion 114 of guide post 112; i.e., that portion of the guide post 112 which extends through guide slot 60.

The second lever 32 includes an elongate first arm 180 having a bored cap 182 at one end, an intermediate first longitudinal rocker groove 184, a second arm 186 having a second longitudinal rocker groove 188 and a second cylindrical nub 190, and a connector portion 192 connecting the first and second arms 180, 186 in parallel such that the rocker grooves 184, 188 are aligned. The rocker grooves 184, 188 are formed in mirror images to rocker grooves 164, 168. The second lever 32 is positioned relative to the lateral punches 20, 22 and assembly frame 26 such that the bored cap 182 also extends over the third portion 124 of the pivot post 118. A clamp band 194 is provided in the circumferential channel 125 of the pivot post to secure the second lever thereover. The first rocker groove 184 of the second lever 32 is engaged about the second portion 148 of guide post 144. The connector portion 192 extends the width of the assembly frame 26 and positions the second arm 186 such that the second rocker groove 188 is engaged about the first portion 146 of guide post 144; i.e,. that portion of the guide post 144 which extends through guide slot 62.

The lever joiner 34 is an elongate member having at each end a linear nub slot 196, 198, each of which is preferably oriented substantially parallel to the channel 14. In addition, one side of the lever joiner includes a protrusion 200. The first nub 170 of the first lever 30 is positioned in nub slot 196, and the second nub 190 of the second lever 32 is positioned in the second nub slot 198. The protrusion 200 extends through medial slot 53 in the second shell portion 52. The handle 28 is fixedly coupled, e.g., by gluing, snap fit or interference fit, to the portion of the protrusion 200 which extends through the medial slot. Therefore, movement of the handle 28 longitudinally through the medial slot 53 causes like movement of the lever joiner 34. In turn, because the pivot bore 162 and bore cap 182 are fixed on the pivot head 126 at pivot bore 63, movement of the lever joiner 34 perpendicular to and toward the channel 14 causes the first and second nubs 170, 190 to slide laterally outward within the nub slots 196, 198, and consequently rotate the levers 30, 32 about the pivot post 118. Rotation of the levers 30, 32 about the pivot post 118 causes the arms 160, 166, 180, 186 at the rocker grooves 164, 168, 184, 188 to provide force to the lateral punches at the guide posts 112, 144. In turn, the guide posts, and lateral punches 20, 22, are moved in an arc through the guide slots 60, 62. Such movement causes the heads 110, 142 of the lateral punches to extend through the vertical slots 65, 66 in the channel wall 64 and into the channel 14.

The support tube 38 is an elongate tube made from a suitable plastically deformable material. One exemplar material is polytetrafluoroethylene (PTFE).

Referring now to FIGS. 1 through 3, in use, the plastically deformable support 38 is positioned over an exterior portion of a guidewire 40, and the support tube is then positioned within the channel 14. The sliding catch 90 is then pushed toward the channel 14, and the center punch 16 is slidably moved along the guide rails 67, 68 such that the head 88 of the center punch extends into the channel. The sliding catch 90 is moved until the catch walls 96, 98 ride over the ramps 70, 72 and lock, such that the center punch 16 is in a position in which the head 88 forces the support tube 38 and guidewire 40 therein into the curving wall portion 61 in the channel 14.

Turning to FIGS. 1, 4 and 5, the handle 28 is next actuated by sliding the handle through the medial slot 53 of the second shell portion 52 toward the channel 14. Such movement causes the lever joiner 34 and levers 30, 32 (FIG. 6) to move the lateral punches 20, 22 such that the heads 110, 142 of the lateral punches 20, 22 enter the channel 14 through the vertical slots 65, 66 in channel wall 64. The lateral punches 20, 22 thereby bend the support tube 38 and guidewire 40 about the head 88 of the center punch 16 into a non-linear configuration. In this manner, the support tube and guidewire are each plastically deformed into a preferred non-linear configuration, which is generally an omega shape.

Figure 9:
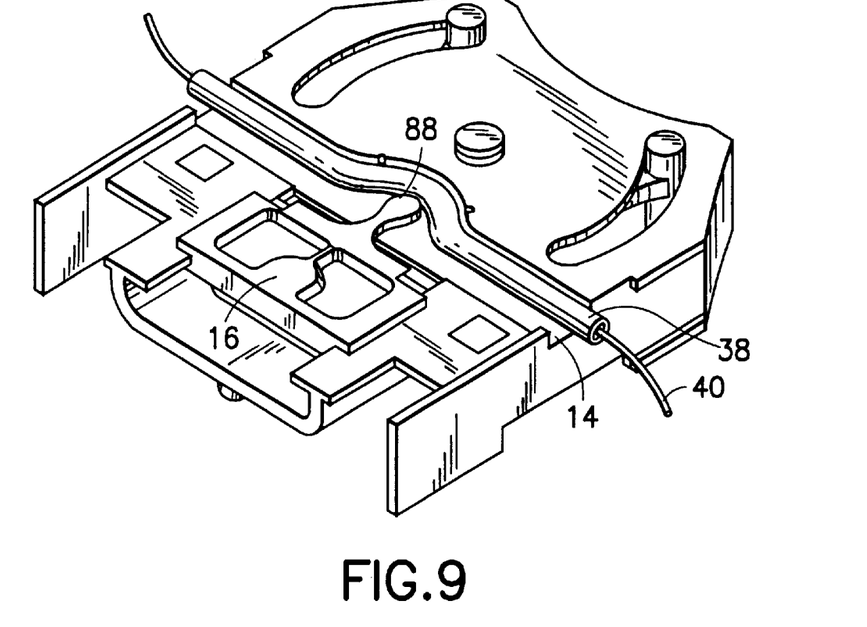
FIG. 9 is a partial top perspective view of the mechanical exchange device, shown in a post-actuation configuration with a support tube and guidewire positioned within a channel of the device.
Figure 10:
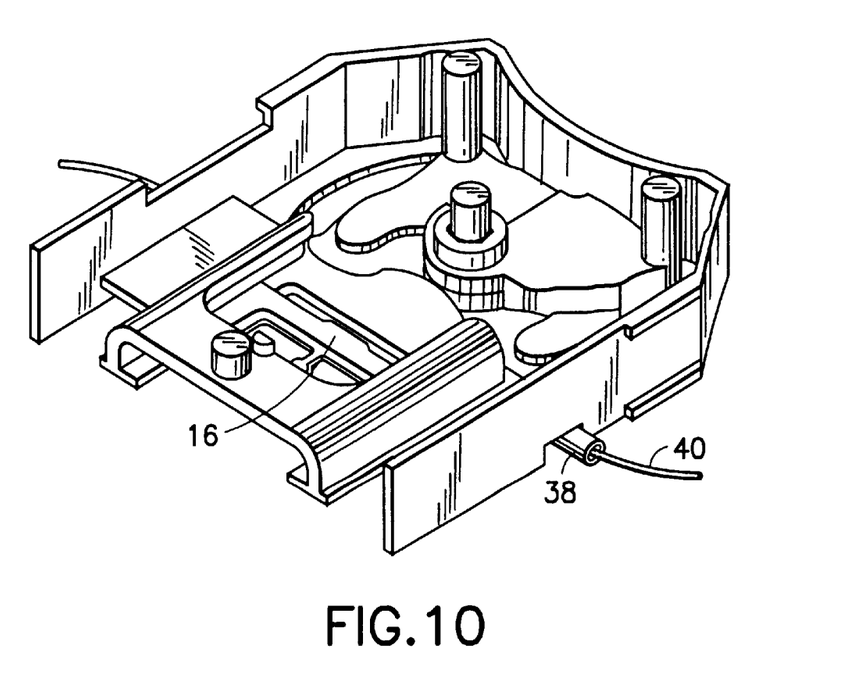
FIG. 10 is a partial bottom perspective view of the mechanical exchange device, shown in a post-actuation configuration with a support tube and guidewire positioned within a channel of the device.

Referring now to FIGS. 1, 9 and 10, the handle 28 is then moved in an opposite direction to remove the heads 110, 142 of the lateral punches from contacting the support tube 38, while the head 88 of the center punch 16, locked in position, prevents the deformed support tube from sliding axially within the channel 14 of the housing.

The non-linear configuration in which the support tube 38 and guidewire 40 have been deformed are such that when a catheter, e.g., a balloon catheter, is moved over the guidewire and through the support tube, the frictional force between the catheter and the guidewire is less than the force required to move the plastically deformed guidewire through the stationary and plastically deformed support tube. Any such non-linear configuration must include a 'critical curve' for the guidewire. A 'critical curve' for a guidewire is defined as a nonlinear path which requires forces greater than the frictional force between a catheter and the guidewire (as the catheter is moved over the guidewire and through the support tube, as described hereinafter) to move the guidewire through the path. A 'critical curve' for a guidewire is related to the modulus of elasticity of the guidewire material(s) and the cross-sectional areas and geometries of the guidewire components. For example, one 'critical curve' for a typical nitinol or stainless steel guidewire with a cross-sectional area of approximately 0.19 $mm^2$ to 0.67 $mm^2$ has been shown to be a pathway defined by the following: a first preferably substantially linear portion extending in a first direction, an arcing second portion which arcs in a direction relative to the first portion preferably through approximately 45° of an approximately 0.5 inch radiused curve, a third arcing portion which arcs in a direction relative the second portion preferably through approximately 90° of an approximately 0.5 inch radiused curve, a fourth arcing portion which arcs in a direction relative to the third portion preferably through approximately 45° of an approximately 0.5 inch radiused curve, and a fifth linear portion preferably substantially parallel to the first portion. That is, an omega shape of the above described size. It will be appreciated that the support tube and guidewire may be plastically deformed into other non-linear configurations which include a 'critical curve'.

Based on the above, as the catheter is advanced or withdrawn through the support tube, axial movement of the guidewire relative to the support tube is inhibited. A catheter may then be fed over the guidewire and into the support tube, i.e., between the support tube and the guidewire, while the guidewire is held in position by the physician or an assistant who holds the housing the device. Alternatively, the housing 12 of the device may be fixed to a support in the vicinity of the surgical field, e.g., at the base 55 by hook and loop fasteners to a surgical table, or even attached directly to the patient. Exchange of a catheter over a guidewire and placement of a new catheter thereover is thereby facilitated.

There have been described and illustrated herein several embodiments of a rapid exchange device. While a particular embodiment of the invention has been described, it is not intended that the invention be limited thereto, as it is intended that the invention be as broad in scope as the art will allow and that the specification be read likewise. Thus, while particular materials for the support tube have been disclosed, it will be appreciated that other materials may be used as well. In addition, while a particular punch configuration (one center, two lateral) has been disclosed, it will be understood that another configuration of two or more punches can be used to deform the support tube and guidewire within into a suitable nonlinear configuration. Also, while a preferred lever system is described to facilitate transfer of handle movement in punch movement, it will be recognized that another system of levers can likewise be used. Furthermore, while the channel is preferably substantially linear, the channel may also be curved throughout. Moreover, while the lateral punches are described as entering the channel around the center punch, the center punch may move completely through the channel and the lateral punches may move toward the center punch on either side of the center punch, yet substantially outside the channel. In addition, the lateral punches may be comprised as a single punch. Also, while a common handle is described for moving the lateral punch, individual handles may be utilized. Furthermore, a common handle may be used to move the center and lateral punches, preferably with the handle causing movement of the center punch prior to movement of the lateral handles. In addition, while not preferable, the center punch may be releasable after being locked in the second position to permit the exchange device to be re-used. It will therefore be appreciated by those skilled in the art that yet other modifications could be made to the provided invention without deviating from its spirit and scope as claimed.

What is claimed is:

1. A rapid exchange device for a guidewire and catheter, comprising:
   a) a housing defining an opening to a channel said channel having a first side and a second side;
   b) a center punch member defining an axis and having a head portion movable between a first position in which said head portion is substantially outside said channel and a second position in which said head portion is moved through said first side of said channel and at least partially into said channel;
   c) first and second lateral punch members located toward said second side of said channel, one on either side of said axis of said center punch member and both movable relative to said center punch member; and
   d) a plastically deformable tube having an exterior diameter sized to be positioned within said channel and an interior diameter sized to receive the guidewire and catheter therethrough,
      wherein when said tube is positioned in said channel and said center punch member is moved into said second position and said first and second lateral punch members are moved relative to said center punch, said tube is plastically deformed into a non-linear configuration by said center punch member and said lateral punch members.

2. A rapid exchange device according to claim 1, further comprising:
   e) a handle coupled to said lateral punch members, said handle operable to move said lateral punch members relative to said center punch member.

3. A rapid exchange device according to claim 2, wherein: said handle is coupled to said lateral punch members with at least one lever.

4. A rapid exchange device according to claim 3, wherein: said at least one lever and said lateral punches are rotatable about a common point.

5. A rapid exchange device according to claim 1, wherein: said center punch member is slidable relative to said housing.

6. A rapid exchange device according to claim 1, wherein: said center punch member is adapted to be locked in said second position.

7. A rapid exchange device according to claim 1, wherein:
each of said lateral punch members includes a head portion which is rotatable relative to said center punch member.

8. A rapid exchange device according to claim 1, wherein:
said lateral punch members are movable through said second side of said channel.

9. A rapid exchange device according to claim 1, wherein:
said housing includes an internal frame member provided with said channel, said housing defines an external opening into said channel, and said center punch member and said lateral punch members are movably coupled to said frame member.

10. A rapid exchange device according to claim 1, wherein:
said channel is substantially linear.

11. A rapid exchange device according to claim 1, further comprising:
e) a guidewire extending at least partially through said tube, said guidewire being plastically deformable by movement of said center punch member and lateral punch members sufficient to cause plastic deformation of said tube.

12. A rapid exchange device according to claim 11, further comprising:
f) a catheter,
wherein when said guidewire is at least partially within said tube and each of said guidewire and said tube are plastically deformed into said non-linear configuration, said catheter is longitudinally movable over said guidewire and through said tube without moving said guidewire relative to said tube.

13. A rapid exchange device according to claim 1, wherein:
said non-linear configuration is omega-shaped.

14. A rapid exchange device for moving a catheter over a guidewire, comprising:
a) a frame defining a channel having a first side and a second side;
b) a first punch member having a first head portion movable between first and second positions, wherein in said first position said first head portion is located substantially to said first side of said channel, and in said second position said first head portion is located at least partially within said channel;
c) a second punch member having a second head portion movable between first and second positions, wherein in said first position said second head portion is located substantially to said second side of said channel, and in said second position said second head portion is located at least partially within said channel;
d) at least one lever coupled to said second punch member; and
e) a handle coupled to said at least one lever and movable into an actuated position which causes said second punch member to move into said second position,
wherein when said first and second punch members are in said respective second positions, said channel and said first and second punch members define a non-linear path into which the catheter may be received.

15. A rapid exchange device according to claim 14, wherein.
said non-linear path is substantially omega-shaped.

16. A rapid exchange device according to claim 14, wherein:
said non-linear path defines a critical curve for the guidewire.

17. A rapid exchange device according to claim 14, further comprising:
f) a tube which when forced into said non-linear path is plastically deformed into a non-linear configuration, said tube having a inner diameter sized to receive a catheter.

18. A rapid exchange device according to claim 17, wherein:
said tube is made from polytetrafluoroethylene (PTFE).

19. A rapid exchange device according to claim 14, further comprising:
f) a third punch member having a third head portion movable between first and second positions, wherein in said first position said third head portion is located substantially to said second side of said channel, and in said second position said third head portion is located at least partially within said channel.

20. A rapid exchange device according to claim 19, wherein:
said second and third punch members are rotatable relative to each other.

21. A rapid exchange device according to claim 19, wherein:
said first punch member defines an axis, and said second and third punch members are located on each side of said axis.

22. A rapid exchange device according to claim 14, wherein:
said first punch member is adapted to be locked in said second position.

23. A rapid exchange device according to claim 14, further comprising:
f) a casing substantially enclosing said first and second punch members and said at least one lever.

* * * * *